United States Patent [19]
Kambara et al.

[11] Patent Number: 5,192,412
[45] Date of Patent: Mar. 9, 1993

[54] ELECTROPHORETIC APPARATUS HAVING ARRAYED ELECTROPHORESIS LANES

[75] Inventors: Hideki Kambara, Hachioji; Keiichi Nagai, Higashiyamato, both of Japan

[73] Assignee: Hitachi, Ltd., Tokyo, Japan

[21] Appl. No.: 800,042

[22] Filed: Nov. 29, 1991

[30] Foreign Application Priority Data

Nov. 30, 1990 [JP] Japan ................................. 2-337074

[51] Int. Cl.$^5$ ........................................... G01N 27/26
[52] U.S. Cl. .............................. 204/299 R; 204/182.8
[58] Field of Search ........................ 204/182.8, 299 R

[56] References Cited

U.S. PATENT DOCUMENTS

| | | | |
|---|---|---|---|
| 3,766,047 | 10/1973 | Elevitch | 204/299 R |
| 4,374,723 | 2/1983 | Vesterberg | 204/299 R |
| 4,675,095 | 6/1987 | Kambara et al. | 204/299 R |
| 4,832,815 | 5/1989 | Kambara et al. | 204/299 R |
| 5,062,942 | 11/1991 | Kambara et al. | 204/299 R |

OTHER PUBLICATIONS

Drossman et al., "High-Speed Separations of DNA Sequencing Reactions by Capillary Electrophoresis", Analytical Chemistry, vol. 62, No. 9, 1990, pp. 900-903.

*Primary Examiner*—John Niebling
*Assistant Examiner*—David G. Ryser
*Attorney, Agent, or Firm*—Antonelli, Terry, Stout & Kraus

[57] ABSTRACT

An electrophoretic apparatus includes an electrophoresis panel having a fluted glass plate and a non-fluted plane plate. The fluted glass plate is provided with a plurality of substantially parallel narrow electrophoresis grooves and a groove intersecting the electrophoresis grooves for laser beam irradiation. The fluted glass plate and the non-fluted plane plate are closely superposed on each other to form many capillaries adapted to be filled with gel to thereby form many electrophoresis lanes. The electrophoretic apparatus further includes a light measuring instrument to measure fluorescence images at positions which are subjected to laser beam irradiation. Passage of fluorescently labeled sampled fragments through the laser beam irradiation positions in each electrophoresis lane is detected by measuring a change of fluorescence emission with time.

21 Claims, 4 Drawing Sheets

ELECTROPHORETIC APPARATUS HAVING ARRAYED ELECTROPHORESIS LANES

BACKGROUND OF THE INVENTION

The present invention relates to an apparatus for separating and detecting fluorescently labeled living samples, such as DNA, by electrophoresis. Examples of such an apparatus include a DNA sequencer and a genetic diagnositc apparatus.

In conventional base sequence determination of DNA, fragments of DNA are labeled by a radioactive element and undergo gel electrophoresis, and then the separation pattern is transferred to a film. This DNA sequencing requires complicated use of radioactive labels, and is furthermore rather laborious and time consuming. To reduce such drawbacks another attempt has been made in which fragments of DNA are fluorescently labeled, and DNA sequencing is conducted by real-time photo detection. A typical example of an electrophoresis analyzing apparatus for DNA sequencing utilizing such real-time photo detection is disclosed in U.S. Pat. No. 4,675,095, in which a plurality of electrophoresis lanes are formed in planar gels (slab gels), and to excite fluorescent lables laser beams are irradiated to the slab gels to cross the electrophoresis lanes.

In Analytical Chemistry, Vol. 62, No. 9, May 1, 1990, pp. 900–903, another attempt has been made in which electrophoresis analysis is achieved on DNA fragments within a gel-filled capillary. According to this technique, the volume to be measured is fairly small, and it is hence expected that this apparatus will be superior in detection sensitivity to the electrophoresis analyzing apparatus which uses slab gels.

In the previously described apparatus utilizing capillary electrophoresis, only one electrophoresis lane can be provide in a capillary. When a plurality of capillaries are arranged, the structure to irradiate excitation light to each capillary and the structure to detect fluorescence from each capillary become rather complicated. It is thus difficult to realize a capillary electrophoresis apparatus with many capillaries which is capable of enhancing analysis throughput. Furthermore, such an apparatus is liable to produce differences in electrophoresis speed among capillaries due to temperature differences therebetween.

SUMMARY OF THE INVENTION

Accordingly, it is an object of the present invention to provide an electrophoretic apparatus which is high in both sensitivity and throughput.

Another object of the present invention is to provide an electrophoretic apparatus which facilitates setting conditions of electrophoresis utilizing a plurality of electrophoresis lanes.

Still another object of the present invention is to provide an electrophoretic apparatus which has a less complicated structure to irradiate excitation light and detect fluorescence than the conventional electrophoretic apparatus, and is hence relatively low in equipment cost.

In view of these and other objects, one aspect of the present invention is directed to an electrophoretic apparatus in which many grooves are formed in one surface of a plane plate made of quartz, glass, etc., and a gel is held in the grooves to thereby form electrophoresis lanes. Each of the grooves serves as a capillary electrophoretic path. More specifically, one aspect of the present invention is directed to an electrophoretic apparatus comprising an electrophoresis panel including first and second plane plates closely contacting to each other, the inner surface of said first plane plate being formed with a plurality of grooves which do not intersect one another and which define gaps adapted to be filled with gel to form a plurality of electrophoresis lanes; voltage applying means for applying an electric field for electrophoresis to said plurality of electrophoresis lanes; and detection means for discretely detecting fragments passing through the electrophoresis lanes at predetermined detection positions in the electrophoresis panel.

It is possible to form at least ten grooves per 1 cm in a quartz or glass plate, and hence 100 or more electrophoresis lanes may be secured in an area 10 cm wide. In the fluorescence detection technique, the detection limit of electrophoresis bands in the electrophoresis lanes depends on the difference in intensity between the background light and fluorescence from objects to be measured. According to the construction of the present invention, the volume of each of the electrophoresis bands can be reduced by decreasing the width of the grooves. For this reason, even a trace amount of fragments may be detected since relatively intense fluorescence is emitted from electrophoresis bands. Thus, an electrophoresis analyzing apparatus with a high detection sensitivity is obtained. Moreover, it possible to set electrophoresis conditions of the electrophoresis lanes since many electrophoresis lanes are closely arranged in an electrophoresis panel.

Typically, the grooves are parallel linear grooves which extend in the first plane plate between opposite first and second edges. Thereof in this mode of the present invention, the voltage applying means applies a voltage between a first buffer solution and a second buffer solution. The first buffer solution communicates at the first edge to the gel within the grooves whereas the second buffer solution communicates at the second edge to the gel within the grooves. The solutions may communicate to the gel within the grooves at positions away from the respective edges of the electrophoresis panel. In this case, it is not necessary to extend the grooves to the first or second edges. Furthermore, the grooves may be cured.

In another aspect of the present invention, the first plane plate is provided with which form electrophoresis lanes, and a linear groove extending in a direction to intersect the grooves. The space of the intersecting groove is filled with the gel, and an excitation light beam passes through this groove for exciting fluorescently labeled fragments.

In still another aspect of the present invention, grooves are formed by attaching a plurality of members in the shape of a ribbon or a wire to the flat surface of one plate. Two plane plates are attached with the ribbon- or wire-like members sandwiched between them. The resulting spaces are filled with a gel to thereby form an electrophoresis panel with electrophoresis lanes.

DETAILED DESCRIPTION OF THE PREFERRED EMBODIMENTS

Figure 1:
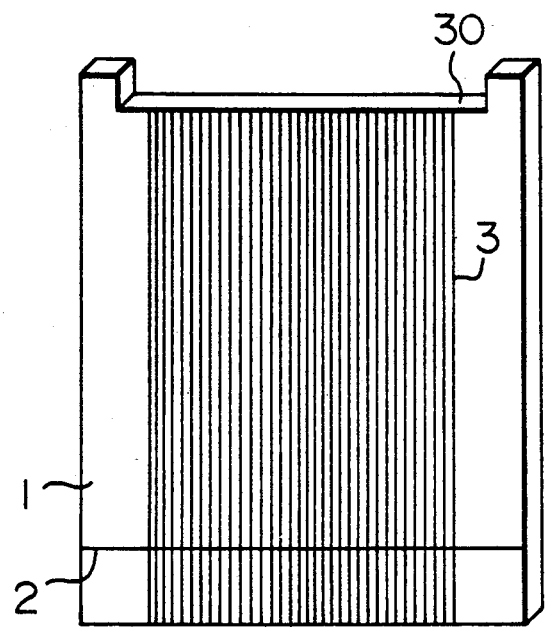
FIG. 1 is a plan view of a fluted glass plate which is one of the essential components of an electrophoretic apparatus according to the present invention.

Referring to FIGS. 1 to 4, one embodiment of the present invention will be described. In FIG. 1, a glass plate 1 which serves as a gel supporting plate has grooves 3 formed in one surface thereof at regular intervals of 1 mm, which grooves have 0.2 mm in width and 0.2 mm in depth. The intervals may be 0.5 mm or smaller. Each of the grooves 3 may be formed to extend from the upper edge to the lower edge of the glass plate 1. The upper edge of the glass plate 1 serves as a sample injection portion, and the upper edge 30 of each of the grooves 3 is diverged. The cross section of the upper edge has a diameter of about 0.5 mm to facilitate sample injection. A groove 2 which has 0.4 mm in width and 0.3 mm in depth is formed in the glass plate 1 at a position 25 cm away from the upper edge thereof so that the groove 2 perpendicularly intersects the grooves 3. The groove 2 reaches to the opposite lateral edges of the glass plate 1.

Figure 2:
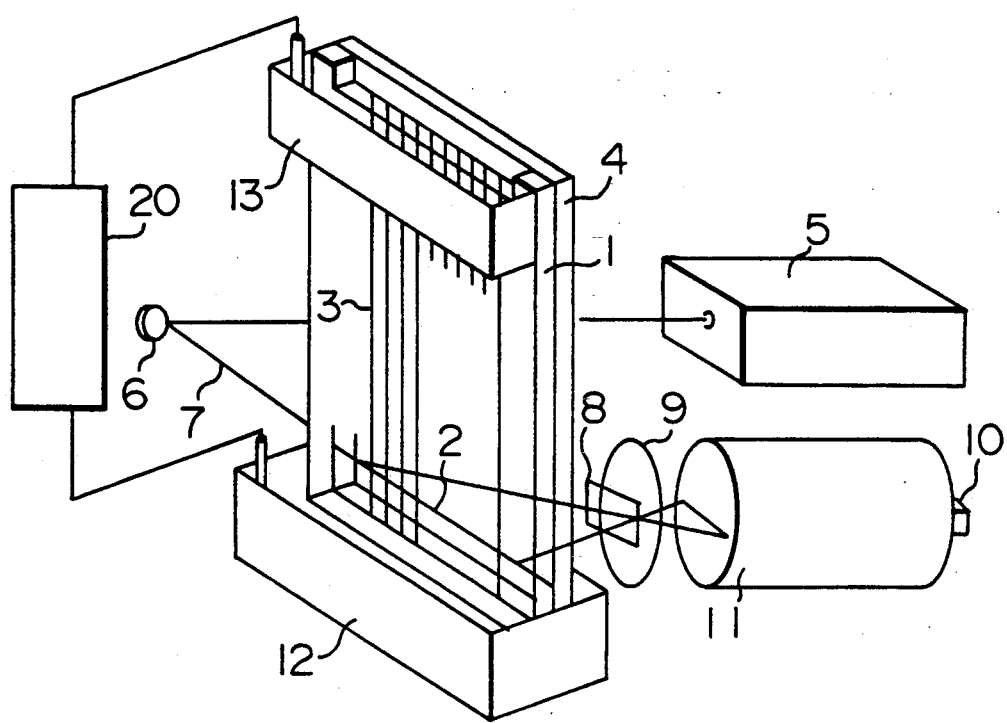
FIG. 2 is a diagrammatic perspective view of an electrophoresis analyzing apparatus according to the present invention using the fluted glass plate of FIG. 1.

As shown in FIG. 2, the glass plate 1 and another non-fluted glass plate 4 are closely superposed on each other with the fluted surface contacting the glass plate 4. Air gaps formed by the grooves 2 and 3 are filled with a polyacrylamide gel. The laminate formed of the glass plates 1 and 4 is used as an electrophoresis panel having a plurality of electrophoresis lanes. The walls of the grooves 3 and the oppositely facing surface of the glass plate 4 define the electrophoresis lanes. The electrophoresis panel is positioned upright, and is provided at an upper portion thereof with an upper buffer tank 13 so that the upper edges of the electrophoresis lanes contact a buffer solution in the upper buffer tank 13. The electrophoresis panel is placed in a lower buffer tank 12 so that the lower edges of the electrophoresis lanes come into contact with the buffer solution in the lower buffer tank 12. A power source 20 is provided to apply an electric field between the buffer solution in the lower buffer tank 12 and the buffer solution in the upper buffer tank 13 for producing an, electrophoresis electric field in each of the electrophoresis lanes. Light beams 7 from an excitation light source 5 are reflected by a mirror 6 to be incident upon one lateral side of the electrophoresis panel so as to pass through the gel in the groove 2. Because of the structure of the electrophoresis panel, the intersections of the electrophoresis lanes with the groove 2 become electrophoresis band detection positions. The fluorescent images from the excitation light irradiation portions of the groove 2 pass through a wavelength selection filter 8, and are then formed on the light receiving surface of an image intensifier 11 by a lens 9. The output image from the image intensifier 11 is detected by a high sensitivity linear sensor 10, such as a diode array, or a two dimensional light detector such as a charge coupled device (CCD). That is, a position discriminable photodetector is provided. Such a structure of the electrophoretic apparatus enables passing of fluorescently labeled sample fragments through the detection positions to be detected for each of the electrophoresis lanes. By passing excitation light beams through the gel in the groove 2, the electrophoresis lanes are uniformly irradiated. Furthermore, detection of the fluorescence in a direction perpendicular to the optical path of the excitation light beam enables detection of fluorescence from sample fragments while suppressing influence of background light.

To analyze a sample such as fluorescently labeled, DNA fragments the sample is added to the gel at the upper ends of the grooves, then the buffer tanks 12 and 13 are filled with buffer solutions, and finally electrophoresis separation is conducted by applying an electrophoresis voltage from the power source 20. In the case where an electrophoresis analysis is to be made on a sample labeled with Texas Red having an excitation maximum wavelength of 596 nm and a light emission maximum wavelength of 615 nm, it is preferable to use a He-Ne laser for the excitation light source 5. In this embodiment, a He-Ne laser, manufactured by Particle Measurement Systems Company, with oscillation wavelength of 594 nm and an output of 2.5 mW was used.

Figure 3:
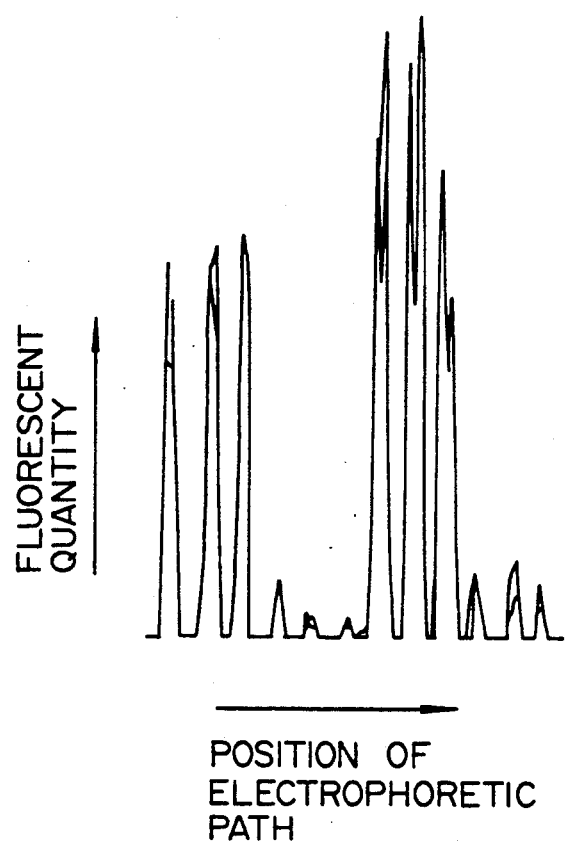
FIG. 3 is a graph illustrating one example of a fluorescent quantity distribution detected by the electrophoresis analyzing apparatus of FIG. 2.
Figure 4:
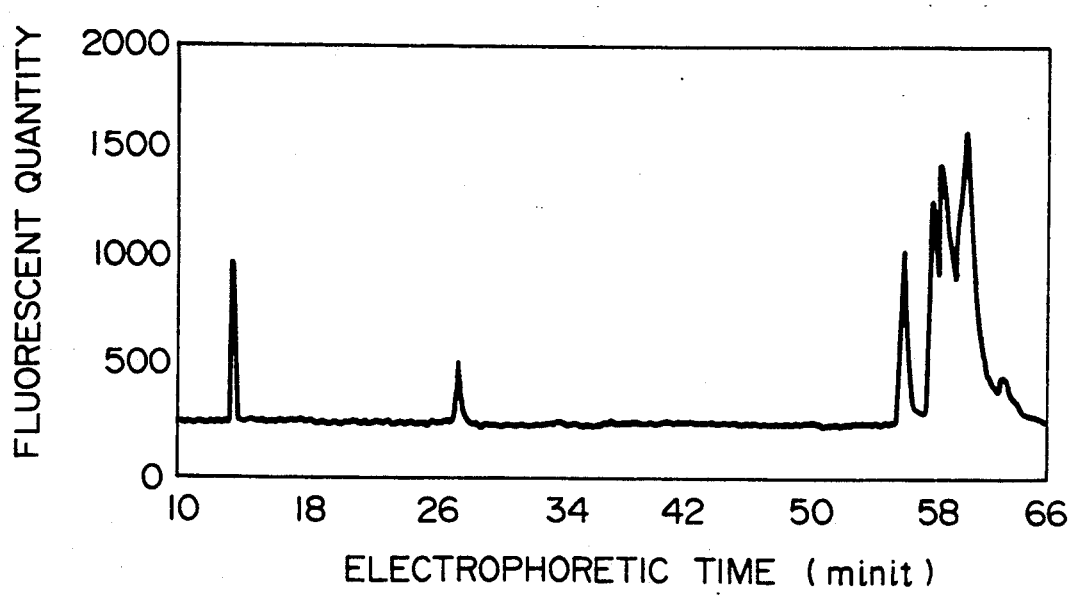
FIG. 4 is a graph showing one example of changes in time of fluorescent quantity at a specific position in the electrophoresis analyzing apparatus of FIG. 2.

FIG. 3 illustrates an intensity distribution of a fluorescent quantity at a time during measurement of fluorescence from electrophoresis lanes through which fluorescently labeled DNA fragments were passing was observed. FIG. 4 shows changes of fluorescence with time which correspond to a DNA fragment spectrum, which fluorescence was emitted from particular electrophoresis lanes when λ phage as a specimen was severed by a limiting oxygen Hind III, and DNA fragments having the severed portions fluorescently labeled were electrophoretically moved. The DNA bands were about 0.7 mm wide and a DNA was contained in a trace amount of $2 \times 10^{-19}$ mole per band, but peaks were detected with an excellent S/N ratio.

Figure 5A:
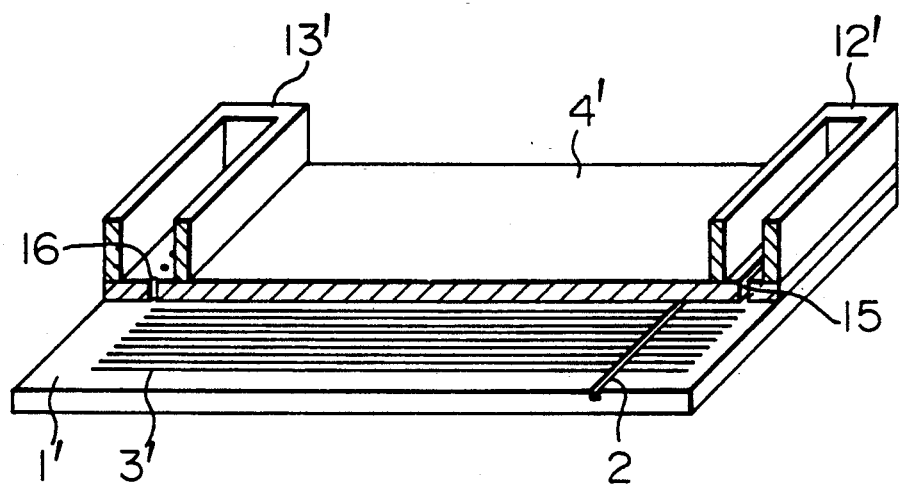
FIGS. 5A and 5B are plan and perspective views of essential parts of another embodiment of the present invention.
Figure 5B:
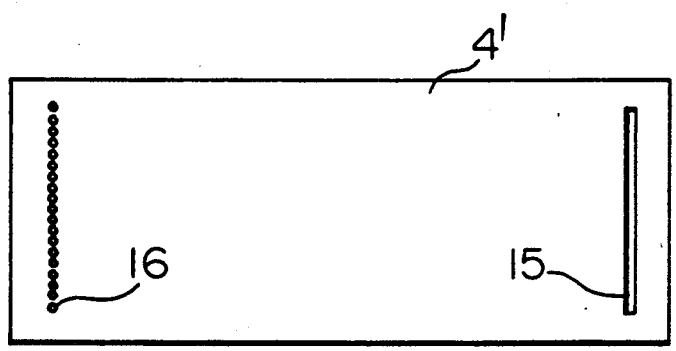

In place of the electrophoresis panel positioned upright, an electrophoresis panel which operates in a horizontal position may be used. FIG. 5A illustrates a horizontal-type electrophoresis panel according to the present invention. The electrophoresis panel is formed by closely attaching a glass plate 1' to another glass plate 4', which glass plate 1' also includes many grooves 3' constituting electrophoresis lanes and a groove 2 for transmitting an excitation light beam. As shown in FIG. 5B, through holes 16 which serve as sample injection ports are formed in the glass plate 4' in the vicinity of the one end thereof to correspond to respective grooves 3'. A rectangular shaped slot 15 is formed in the glass plate 4' near the other end thereof to communicate to the grooves 3' to allow electrophoresis fragments to flow out. After the glass plates 1' and 4' are attached together, a gel is charged into a gap between the plates, the grooves, the slot 15, and the through holes 16 for forming a plurality of electrophoresis lanes. A frame member 13' is secured to the glass plate 4' around the holes 16 for forming a buffer tank while a frame member 12' is mounted to the glass plate 4' around the slot 15 for forming another buffer tank. The grooves 3' are formed to extend between positions which correspond to the sample injection holes 16 and the fragment outlet slot 15. The grooves 3' may however, extend between the opposite ends of the glass plate 1' as in the embodiment of FIG. 1. In either case, the electrophoretic paths extend between the sample injection holes 16 and the fragment outlet slot 15. Samples are injected with ease since the sample injection holes 16 are provided in one principal plane of the glass plate 4' instead of being provided at the end surface thereof. After sample solutions to be analyzed are injected into the respective sample injection holes 16, each of the buffer tanks are filled with a buffer solution, electrophoresis is conducted by applying a voltage, and then passage of fragments is detected by irradiating laser beams to the groove 2.

In the preceding embodiments, quartz glass, heat resistant glass or the like is suitably used to make the two plates which constitute the electrophoresis panel. Any electrically insulated plates having good heat conductivity to some extent may be used as the electrophoresis panel plates. When an etchable light sensitive glass is used, many grooves may be accurately formed by etching with good reproducibility. Even electrically conductive plates may be used if the surfaces of the plates are coated with an insulating material after the grooves are formed. For example, a metallic plate coated with an insulating layer such as an oxide film or a nitride film may be used as one of the electrophoresis panel plates to advantageously dissipate heat generated due to electrophoresis.

Figure 6:
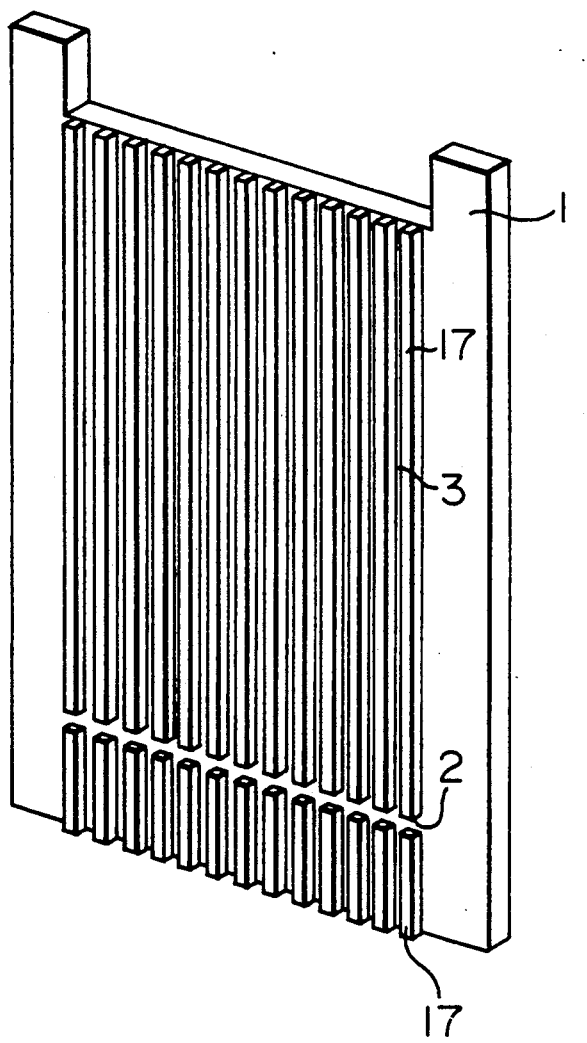
FIG. 6 is a perspective view of an essential part of still another embodiment of the present invention.

In the preceding embodiments, spaces serving as electrophoresis lanes are secured by forming grooves in plane plates 1 and 1'. Alternatively, another structure in which many parallel spacers are sandwiched between the plane plates may be adopted. FIG. 6 illustrates one of the electrophoresis panel plates having such a structure. To one surface of the glass plate 1 are attached two rows of ribbons 17 having a uniform thickness at regular fine intervals. Grooves 3 are defined between adjacent ribbons 17 and 17. Two rows of the ribbons 17 are separated at a particular position to form a linear groove 2 which intersects the grooves 3. The ribbons 17 may be made of a polymer such as polyethylene telephthalate and an acrylic resin. The glass plate 1 with the ribbons 17 has a surface which is similar in shape to that of the glass plate shown in FIG. 1, and may be used as one of the electrophoresis panel plates of FIG. 2. That is, the ribbons 17 serve as spacers for the two plates and also serve to discretely separate a plurality of electrophoresis lanes. In place of ribbons 17, wire-like members may be used, and may be made of glass, other electrically insulating materials, or high electrical resistance material other than a polymer.

In the preceding embodiments, the electrophoresis medium which fills the grooves is not limited to a polyacrylamide gel, but may be a gel such as agarose. Instead of gels, an electrically conductive liquid or solution may be used as the electrophoresis medium.

In place of the structure in which excitation light beams traverse the plurality of electrophoresis lanes as shown in FIG. 1, another structure in which the electrophoresis lanes are adapted to be sequentially scanned by a moving excitation light beam may be adopted. In this case, the lateral groove 2 need not be provided. More specifically, the structure may be such that whether or not sample fragments exist at particular positions corresponding to groove 2 in the electrophoresis lanes is detected.

According to the present invention, it is possible to reduce the cross-sectional area of each of the electrophoresis lanes, and hence measurement may be conducted for trace amounts of samples. In the conventional DNA measurement using a planar-type gel which is 0.3 to 0.5 mm thick, the width of each of the electrophoresis lanes or width of the DNA bands is 2 to 5 mm. That is, the smallest cross-sectional area of the electrophoresis lanes is about 0.6 $mm^2$. In the embodiments of the present invention, the cross-sectional area of the electrophoresis lanes is about 0.04 $mm^2$, and it is possible to reduce the cross-sectional area to 0.01 $mm^2$ or below by further reducing the width of the grooves. It is even possible to measure trace amounts of samples of one or two figures by reducing the cross-sectional area. The pitch of the electrophoresis lanes may be further reduced, and it is thus possible to obtain an electrophoresis panel having more than 100 electrophoresis lanes, thereby improving the throughput of the analysis.

In DNA sequencing four groups of DNA fragments, of which terminal bases include adenine (A), cytosine (C), guanine (G) and thymine (T) are prepared on the basis of the DNA sample to be analyzed, and then separately undergo electrophoresis. In the case where groups of DNA fragments are placed into respective electrophoresis lanes, it is desirable to make conditions of the electrophoresis lanes equal. According to the present invention, many electrophoresis lanes are closely formed in an electrophoresis panel, and differences in temperature between the electrophoresis lanes become small, with the result that differences in electrophoresis speed are less likely to be produced than in the conventional electrophoresis apparatuses.

What is claimed is:

1. An electrophoretic apparatus comprising:
    an electrophoresis panel including first and second plane plates, a principal surface of said first plane plate being in close contact with said second plane plate and being provided with a plurality of lengthwise grooves which do not intersect one another and a widthwise groove intersecting said lengthwise grooves and extending to opposite edges of said principal surface of said first plane plate, said lengthwise grooves defining gaps adapted to be filled with an electrophoresis medium to provide a plurality of electrophoresis lanes;
    voltage applying means for applying an electric field for electrophoresis to said plurality of electrophoresis lanes; and
    detection means for discretely detecting fragments passing through the electrophoresis lanes at predetermined detection positions in the electrophoresis panel.

2. An electrophoretic apparatus as recited in claim 1, wherein gel is filled in said gaps defined by said lengthwise grooves.

3. An electrophoretic apparatus as recited in claim 1, wherein said lengthwise grooves extend to opposite edges of the principal surface of the first plane plate.

4. An electrophoretic apparatus as recited in claim 1, wherein said lengthwise grooves are linear and parallel to one another.

5. An electrophoretic apparatus as recited in claim 1, wherein at least one of said first and second plane plates is made of a glass material.

6. An electrophoretic apparatus as recited in claim 1, wherein at least one of said first and second plane plates is a metal plate having at least surface coated with an electrically insulating material.

7. An electrophoretic apparatus as recited in claim 1, wherein a width of each of said lengthwise grooves is not greater than 0.2 mm.

8. An electrophoretic apparatus as recited in claim 7, wherein a cross-sectional area of each of said electrophoresis lanes is not greater than 0.04 mm².

9. An electrophoretic apparatus as recited in claim 1, wherein a number of said lengthwise grooves per 1 cm is at least ten.

10. An electrophoretic apparatus comprising:

an electrophoresis panel including first and second plane plates in close contact with each other, a principal surface of said first plane plate being in close contact with said second plane plate and being provided with a plurality of lengthwise grooves which do not intersect one another and a widthwise groove intersecting said lengthwise grooves and extending to opposite edges of said principal surface of said first plane plate, said lengthwise grooves defining gaps adapted to be filled with an electrophoresis medium to provide electrophoresis lanes in the respective lengthwise grooves;

voltage applying means for applying an electric field for electrophoresis to the plurality of electrophoresis lanes to thereby electrophoretically move fluorescently labeled sample fragments in the electrophoresis lanes;

excitation means for passing at least one light beam from one side of the electrophoresis panel along said widthwise groove for exciting said fluorescently labeled sample fragments to produce fluorescent emissions; and light detection means for detecting said fluorescent emissions from the sample fragments at said widthwise groove for the respective electrophoresis lanes.

11. An electrophoretic apparatus as recited in claim 10, wherein said light detection means includes position discriminable light detection means disposed to detect said fluorescent emissions along said widthwise groove in a direction substantially perpendicular to an optical path of said at least one light beam extending along said widthwise groove.

12. An electrophoretic apparatus as recited in claim 10, wherein said gaps defined by said lengthwise grooves are filled with gel serving as said electrophoresis medium.

13. An electrophoretic apparatus as recited in claim 10, wherein said lengthwise grooves extend to opposite edges of said principal surface of said first plane plate.

14. An electrophoretic apparatus as recited in claim 10, wherein said lengthwise grooves are linear and parallel to one another.

15. An electrophoretic apparatus as recited in claim 10, wherein at least one of said first and second plane plates is made of a glass material.

16. An electrophoretic apparatus as recited in claim 10, wherein at least one of said first and second plane plates is a metal plate having at least one surface coated with an electrically insulating material.

17. An electrophoretic apparatus as recited in claim 10, wherein a width of each of said lengthwise grooves is not greater than 0.2 mm.

18. An electrophoretic apparatus as recited in claim 17, wherein a cross-sectional area of each of said electrophoresis lanes is not greater than 0.04 mm².

19. An electrophoretic apparatus as recited in claim 10, wherein a number of said lengthwise grooves per 1 cm is at least ten.

20. An electrophoretic apparatus comprising:

an electrophoresis panel including two plates sandwiching therebetween spacers which are arranged in two rows at predetermined intervals in each of said two rows and are in the shape of one of a ribbon and a wire, and an electrophoresis medium filled in spaces defined by said two plates and said spacers to thereby provide a plurality of lengthwise electrophoresis lanes extending between said spacers, and a widthwise lane extending between said two rows in which said spacers are arranged and intersecting said lengthwise electrophoresis lanes;

voltage applying means for applying an electric field for electrophoresis to the plurality of lengthwise electrophoresis lanes; and detection means for discretely detecting fragments passing through the lengthwise electrophoresis lanes at predetermined detection positions in the electrophoresis panel.

21. An electrophoretic apparatus comprising:

an electrophoresis panel including a first plane plate to which spacers in the form of one of a ribbon and a wire are attached in two rows at predetermined intervals in each of said two rows, and a second plane plate disposed on said spacers, said first and second plane plates and said spacers defining spaces adapted to be filled with an electrophoresis medium to form a plurality of lengthwise electrophoresis lanes extending between said spacers, and a widthwise lane extending between said two rows in which said spacers are arranged and intersecting said lengthwise electrophoresis lanes;

voltage applying means for applying an electric field for electrophoresis to said plurality of lengthwise electrophoresis lanes; and detection means for discretely detecting fragments passing through said plurality of lengthwise electrophoresis lanes at predetermined detection positions in the electrophoresis panel.

* * * * *